United States Patent [19]

Beevor

[11] Patent Number: 4,782,186

[45] Date of Patent: Nov. 1, 1988

[54] CONDENSATION OF ALDEHYDES

[75] Inventor: Robert G. Beevor, Twickenham, England

[73] Assignee: British Petroleum Company p.l.c., London, England

[21] Appl. No.: 911,052

[22] Filed: Sep. 24, 1986

[30] Foreign Application Priority Data

Oct. 15, 1985 [GB] United Kingdom ............... 8525402

[51] Int. Cl.$^4$ ................................................ C07C 45/45
[52] U.S. Cl. ................................................ 568/388
[58] Field of Search ........................................ 568/388

[56] References Cited

U.S. PATENT DOCUMENTS

| | | | |
|---|---|---|---|
| 4,301,310 | 11/1981 | Wagner | 568/388 |
| 4,326,086 | 4/1982 | Mohring et al. | 568/388 |
| 4,358,619 | 11/1982 | Stemmler et al. | 568/388 |

FOREIGN PATENT DOCUMENTS

| | | | |
|---|---|---|---|
| 59-164746 | 9/1984 | Japan | 568/388 |
| 59-164745 | 9/1984 | Japan | 568/388 |
| 60-184038 | 9/1985 | Japan | 568/388 |

OTHER PUBLICATIONS

Matsumoto et al, J. Org. Chem., vol. 50, pp. 603–606 (1985).

*Primary Examiner*—James H. Reamer
*Attorney, Agent, or Firm*—Nixon & Vanderhye

[57] ABSTRACT

A liquid phase process for preparing alpha-hydroxyketones is provided. The process comprises condensing one or more aldehydes in the presence of a thiazolium salt and a sterically hindered base having a pKa value greater than 12.0. The sterically hindered base is preferably either an amidine or a secondary or tertiary alkoxide of an alkali metal.

10 Claims, No Drawings

CONDENSATION OF ALDEHYDES

The present invention relates to the condensation of aldehydes in the presence of a thiazolium salt and a sterically hindered base, specifically a base having a pKa value above 12.0.

It is known from J. Org. Chem., 1985, 30, pp 603 et seq that formaldehyde can be reacted with another aldehyde in the presence of a thiazolium salt and triethylamine. The final product of the reaction is a 1-hydroxy-2-one type of compound.

It has now been found that the rate of condensation of aldehydes and the selectivity to the desired product can be significantly improved by the use of a strong, sterically hindered base.

Accordingly, the present invention provides a process for the production of alpha-hydroxyketones by condensation of one or more aldehydes in the presence of a thiazolium salt and a base characterised in that the base is a sterically hindered base having a pKa value greater than 12.0.

The base used in the process of the present invention is one which has a pKa value of greater than 12.0, as measured in water at 25° C., and is one which is sterically hindered. Sterically hindered bases are defined as either those bases which have at least one secondary or tertiary carbon atom directly bonded to one of their sites of basicity or amidines. Preferably the sterically hindered base comprises either a secondary or tertiary alkoxide of an alkali metal or an amidine.

By the term amidine is meant a compound containing the grouping

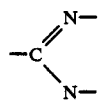

Conveniently the free valencies of the nitrogen atom are attached to carbon atoms or hydrogen and the free valency on the carbon to another carbon or nitrogen atoms. In the last mentioned case the structure comprises a guanidine grouping.

A preferred class of amidines is the cyclic amidines. Cyclic amidines are defined as those amidines wherein at least one of the nitrogen atoms is part of an alicyclic or heterocyclic substituted or unsubstituted hydrocarbyl ring. In the case where the amidine is a guanidine then any two of the three nitrogen atoms may be in the same or different rings. Those nitrogen atoms which are not part of any such ring may form part of a substituted or unsubstituted hydrocarbyl group. Polymer supported amidines can also be used.

A preferred class of cyclic amidines is that in which the amidine group can form part of a fused ring system containing 6 and 5 membered rings or 6 and 7 membered rings or two six membered rings.

Specific examples of the alkali metal alkoxide include sodium isopropoxide and potassium tertiary butoxide (pKa=greater than 16) and those of the amidines include 1,5-diazabicyclo(4.3.0)non-5-ene (pKa=ca 12.8) 1,8-diazabicyclo[5.4.0]undec-7-ene (pKa=12.8) and 1,5,7-triazabicyclo-[4.4.0]dec-5-ene (pKa=13.5).

The term alpha-hydroxyketone is defined as meaning any ketone which has one or more hydroxyl groups on a carbon atom adjacent to the carbonyl group of the ketone. Included in such a definition are both alpha-monohydroxyketones and alpha-dihydroxyketones. In the case of dihydroxyketones the hydroxyl groups may be on the different carbon atoms.

In principle any aldehyde may be condensed. The condensation may either be a self-condensation where one or more molecules of the same aldehyde condense or it may be a cross-condensation involving two or more aldehydes. Typical examples include the cross-condensation of formaldehyde and acetaldehyde to generate hydroxyacetone and the self-condensation of three molecules of formaldehyde to produce 1,3-dihydroxyacetone. Where the reaction is a cross-condensation it is preferable that one of the aldehyde reactants used is formaldehyde.

When formaldehyde is a reactant either the monomeric form or a suitable oligomer or polymer may be used. For cross-condensations the different aldehydes are preferably present in approximately equimolar amounts.

Irrespective of whether it is a self-condensation or cross-condensation, the molar ratio of the aldehyde reactant(s) to the sterically hindered base is suitably in the range 100:1 to 1:1, preferably 20:1 to 5:1.

The thiazolium salt used may be an alkyl, aralkyl, alkaryl or an aryl thiazolium salt. The thiazolium salt is preferably a thiazolium halide, for example 3-ethylbenzothiazolium bromide. The molar ratio of the thiazolium salt to the sterically hindered base is preferably 1:1. The thiazolium salt can be used in supported form i.e. bonded to an inert polymer backbone.

The condensation is conveniently carried out in a solvent which is inert under the reaction conditions. Examples of solvents are alcohols ethers and amides.

The condensation is suitably carried out at a temperature in the range 20°–150° C., preferably in the range 40°–100° C. It is preferable to carry out the condensation under an inert atmosphere such as nitrogen, argon, helium etc.

The alpha-hydroxyketones produced by the process of the present invention are useful as solvents, starting materials for organic synthesis or as gasoline supplements.

The present invention is further illustrated with reference to the following Examples and Comparative Tests.

EXAMPLE 1

A solution of acetaldehyde (15.0 mmol), formaldehyde (15.0 mmol), 1,5,7-triazabicyclo-[4.4.0]dec-5-ene, (1.5 mmol), and 3-ethylbenzothiazolium bromide (1.5 mmol) in dry ethanol (14 cm$^3$) was heated to 60° C. in a sealed tube, with stirring, for one hour then cooled in an ice/water bath. Analysis of the liquid product indicated a 43.5% conversion of acetaldehyde with selectivities of 91.0% to hydroxyacetone and 7.4% to 3-hydroxybutanone.

EXAMPLE 2

Example 1 was repeated except that 1.5 mmol of 1,8-diazabicyclo-[5.4.0]undec-7-ene was used as the base. Gas chromatography of the liquid product showed a 40.5% conversion of acetaldehyde with selectivities of 86.0% to hydroxyacetone and 8.2% to hydroxybutanone.

EXAMPLE 3

Example 1 was repeated except that 1.5 mmol of potassium t-butoxide was used as the base. Analysis of the liquid product showed a 41.1% conversion of acetaldehyde with selectivities of 85.2% to hydroxyacetone and 7.4% to hydroxybutanone.

EXAMPLE 4

Example 1 was repeated in the absence of formaldehyde. Analysis of the liquid product showed a 45.9% conversion of acetaldehyde with a selectivity to hydroxybutanone of 52.9%.

EXAMPLE 5

Example 1 was repeated using 1,3,5-trioxan as the source of formaldehyde. Analysis of the liquid product showed a 40.8% conversion of acetaldehyde with selectivities of 27.2% to hydroxyacetone and 34.3% to hydroxybutanone.

COMPARATIVE TEST A

Example 1 was repeated except that triethylamine (1.5 mmol) (pKa=11) was used instead of the guanidine base. Analysis of the liquid product by gas chromatography showed a 24.9% conversion of acetaldehyde with selectivities of 84.5% to hydroxyacetone and 4.8% to hydroxybutanone.

COMPARATIVE EXAMPLE B

Paraformaldehyde (6.0 mmol), 3-ethylbenzothiazolium bromide (0.3 mmol), triethylamine (0.3 mmol), and 1,4-dioxan (2.0 cm$^3$) were heated to 90° C. in a sealed tube for 10 minutes then cooled in an ice/water bath. Analysis of the liquid product showed a 22.2% conversion of formaldehyde with selectivity to 1,3-dihydroxyacetone of 72.5%.

EXAMPLE 6

Comparative Example B was repeated except that 1, 5, 7-triazabicyclo [4.4.0]-dec-5-ene (0.3 mmol) was used in place of triethylamine. Analysis of the liquid product showed a 32.8% conversion of formaldehyde with selectivity of 79.7% to 1,3-dihydroxyacetone.

EXAMPLES 7-10

Example 1 was repeated except that the acetaldehyde was replaced by the appropriate aldehyde. The results obtained were as follows:

| Example | Aldehyde (RCHO) | RCHO Conversion | Selectivity to RCOCH$_2$OH |
|---|---|---|---|
| 7 | C$_2$H$_5$CHO | 17.6 | 97.9 |
| 8 | (CH$_3$)$_2$CHCHO | 28.2 | 96.0 |
| 9 | C$_6$H$_5$CHO | 45.7 | 98.1 |
| 10 | HOCH$_2$CHO | 12.1 | 89.2 |

I claim:

1. In a process for the production of an alpha-hydroxyketone by condensation of one or more aldehydes in the presence of a thiazolium salt and a base at a temperature in the range 20°–150° C. the improvement which comprises using, as base, a sterically hindered base having a pKa value greater than 12.0.

2. A process as claimed in claim 1 wherin the sterically hindered base is an amidine.

3. A process as claimed in claim 2 wherein the amidine is a cyclic amidine.

4. A process as claimed in claim 2 wherein the amidine is a guanidine.

5. A process as claimed in claim 3 wherein the cyclic amidine is a cyclic guanidine.

6. A process as claimed in claim 3 wherein the cyclic amidine has an amidine group which forms part of a fused ring system containing 6 and 5 membered rings, or 6 and 7 membered rings or two six membered rings.

7. A process as claimed in claim 6 wherein the cyclic amidine is selected from the group consisting of 1,5-diazabicyclo[4.3.0]non-5-ene, 1,8-diazabicyclo[5.4.0]undec-7-ene and 1,5,7-triazabicyclo-[4.4.0]dec-5-ene.

8. A process as claimed in claim 1 wherein the sterically hindered base is a secondary or tertiary alkoxide of an alkali metal.

9. A process as claimed in claim 8 wherein the sterically hindered base is either potassium tertiary butoxide or sodium isopropoxide.

10. A process for the production of 1,3-dihydroxyacetone which comprises self-condensing formaldehyde at a temperature in the 20° to 150° C. in the presence of a thiazolium salt and a sterically hindered base having a pKa value grater than 12.0.

* * * * *